United States Patent
Zhang (10) Patent No.: US 11,273,240 B2
(45) Date of Patent: Mar. 15, 2022

(54) MILK SUCTION AND COLLECTION DEVICE

(71) Applicant: Shu Ting Zhang, Jingshan (CN)

(72) Inventor: Shu Ting Zhang, Jingshan (CN)

(*) Notice: Subject to any disclaimer, the term of this patent is extended or adjusted under 35 U.S.C. 154(b) by 364 days.

(21) Appl. No.: 16/675,734

(22) Filed: Nov. 6, 2019

(65) Prior Publication Data

US 2021/0030934 A1   Feb. 4, 2021

(30) Foreign Application Priority Data

Aug. 2, 2019  (CN) .......................... 201910713290.7

(51) Int. Cl.
*A61M 1/06* (2006.01)

(52) U.S. Cl.
CPC ....... *A61M 1/062* (2014.02); *A61M 2209/084* (2013.01)

(58) Field of Classification Search
CPC ........ A61M 1/06; A61M 1/062; A61M 1/064; A61M 1/082; A61M 3/0262
See application file for complete search history.

(56) References Cited

U.S. PATENT DOCUMENTS

| | | | | |
|---|---|---|---|---|
| 3,670,730 A | * | 6/1972 | White ................... | A61J 7/0053 604/207 |
| 4,705,504 A | * | 11/1987 | Viers ...................... | A61M 1/06 604/75 |
| 6,440,100 B1 | | 8/2002 | Prentiss | |
| 2004/0015127 A1 | | 1/2004 | Silver | |
| 2018/0041365 A1 | | 2/2018 | Anthony et al. | |
| 2018/0154055 A1 | | 6/2018 | Alvarez | |
| 2020/0086019 A1 | * | 3/2020 | Chua ....................... | A61M 1/06 |

FOREIGN PATENT DOCUMENTS

| | | |
|---|---|---|
| CN | 206949576 U | 2/2018 |
| CN | 207722082 | 8/2018 |
| CN | 209378118 U | 9/2019 |
| CN | 210963275 U | 7/2020 |
| WO | 2018041365 A1 | 3/2018 |

OTHER PUBLICATIONS

European Patent Application No. 19213952.5 extended European search report dated Jun. 16, 2020.

* cited by examiner

*Primary Examiner* — Nathan R Price
*Assistant Examiner* — Courtney B Fredrickson
(74) *Attorney, Agent, or Firm* — Michael Best & Friedrich LLP (57) ABSTRACT

Disclosed is a milk suction and collection device integrally manufactured and formed by silicone. The milk suction and collection device includes a main body which is hollow inside to define a milk storage chamber and is further provided with a milk pouring port operative to be selectively blocked. A breast protecting film is provided on a side in a thickness direction of the main body and is configured to be fitted with an outer periphery of a breast, and is further provided with a milk collecting port communicating with the milk storage chamber. The side of the main body of the milk suction and collection device provided with the breast protecting film is operative to be fitted with the breast because the milk suction and collection device is integrally manufactured and formed by silicone. When the milk pouring port is closed, a breast pumping function is achieved by squeezing the main body. When the milk pouring port is opened, a milk collecting function is achieved.

20 Claims, 3 Drawing Sheets

MILK SUCTION AND COLLECTION DEVICE

CROSS-REFERENCE TO RELATED APPLICATIONS

This application is a U.S. application which claims the priority of China patent application No. 201910713290.7 filed on Aug. 2, 2019, the disclosure of which is hereby incorporated herein by reference in its entirety.

TECHNICAL FIELD

The present disclosure relates to the technical field of mother and infant products, and more particularly relates to a wearable milk suction and collection device with a dual function breast pumping and milk collecting.

BACKGROUND

Breast pumping devices available on the current market can be roughly divided into two categories: manual breast pumps and electric breast pumps.

A conventional manual breast pump typically includes a three-way connector, a breast pumping cover, and a squeezing handle. The breast pumping cover is used for covering a user's breast and is connected to one of the three-way connector's ports. Another port of the three-way connector is used for mounting the squeezing handle. The last port of the three-way connector is used for connecting to a milk bottle. In use, the milk bottle is installed on the three-way connector, the breast pump cover is covered on the user's breast, then the squeezing handle is operated to continuously pump out the air in the breast pump cover, so that a negative pressure is created inside the breast pump cover to squeeze the breast, thereby expressing the milk in the breast. Existing manual breast pumps have the following defects. First, to enable the breast pump cover to be well connected to the three-way connector, the breast pump cover is usually made of a hard plastic, which however would make the user very uncomfortable when it is directly attached to the human body. To improve the comfort, in some cases a silicone layer is attached to the interior of the breast pump cover to isolate the skin from the hard plastic. However, the overall shape cannot be changed, while different users' breasts come in different shapes and sizes and even the same person's breast would undergo a big size change before and after breast pumping. As such, in the later stage of breast pumping the breast pump cover would not be able to automatically change its shape to fit the breast, resulting in poor sealing thereby affecting the milk suction effect. Second, the various components and parts are arranged in a complicated structure, and a three-way connector and a squeezing handle need to be arranged, which increases the difficulty for assembly, cleaning, and disinfection. Third, the milk collecting function is absent, so that a milk anti-overflow pad needs to be additionally prepared to prevent the milk of a lactating woman's breast from overflowing to wet clothes.

An electric breast pump includes a main body (an air pump), a three-way connector, and a breast pump cover. In some existing electric breast pumps, the three-way connector and the breast pump cover are of an integrated structure, and an air suction port of the main body is connected to the three-way connector via an air pipe. Before use, all accessories need to be assembled as required and then connected to a milk bottle. The electric breast pump is secured on the breast in a handheld manner or with the assistance of a breast feeding bra. Then a power supply of the main body is turned on and the electric breast pump starts to generate a suction force entering the milk expressing process. Existing electric breast pumps have the following defects. First, in the case any one of the accessories is damaged or fails, the electric breast pump would not be able to achieve the normal milk suction effect. Second, the accessories come in a large number, resulting in a complicated assembly before using the electric breast pump, thereby costing a lot of time for the user, and the cleaning post the use of electric breast pump also takes much time. Furthermore, the three-way connector has a small size, easily leading to dead corners, where bacteria are prone to grow thus posing hidden threats for the user's health. Third, breast pump cover is mainly made of PP (polypropylene) which has a hard texture and is not deformable. This would easily cause an impact feel on the user's breast. Furthermore, it is also difficult to be fitted with different women's breasts, such that gaps would easily be created resulting in air leakage hence an unsatisfactory milk suction effect. Forth, the electric power cannot be started and stopped immediately. For example, if the user forgets to press the stop button on the condition that there is no milk in the breast, then the breast would be susceptible to damage. In severe cases, it would cause bleeding of the breast. Fifth, similar to a manual breast pump, the electric breast pump only has a breast pumping function and lacks a milk collecting function.

In addition, a silicone breast pump is also available on the market. The silicone breast pump includes a breast pumping head, a bottle neck, and a bottle body, where these three components are usually formed by an integral manufacturing method. The integrally manufactured silicone breast pump usually has a designed height of 15 to 18 cm, a width of 8 to 10 cm, a weight of 75 to 85 g and a capacity of 90 to 150 ml, and has the following defects. the first, it has a large size and heavy weight. As the use proceeds, the suction force of the breast pumping head would be reduced as the weight of the breast pump as a result of the secretion of milk. In an alternative case, due to the deformation of the breast after the milk is pumped out, air leakage may occur at the contacting surface between the breast and the silicone breast pump. In another alternative case, the silicone breast pump may not be used in a correct way leading to an improper operation thereby easily causing the separation of the breast pump from the breast so that the silicone breast pump would fall off. Second, the breast pump has a large size making it not easy to hide it in the clothes. When the breast pump is used in an exposed state, the user's breast would be exposed because the breast pumping head is transparent. That means the breast pump can only be used in a relatively hidden place making it inconvenient to use. Third, the breast pump only has the breast pumping function and lacks the milk collecting function.

SUMMARY

One object of embodiments of the present disclosure is to provide a milk suction and collection device featuring a simple structure, an integrated structure, a small number of parts, and ease of operation without needing assembly.

Another object of the embodiments of the present disclosure is to provide a milk suction and collection device that is able to provide not only a breast pumping function but also a breast connecting function.

Another object of the embodiments of the present disclosure to provide a milk suction and collection device featuring a simple structure, a small size, lightweight, small damage to breasts, and a well fit with the breast enabling it not susceptible to falling off.

To achieve these objects, embodiments of the present disclosure adopt the following technical solutions.

There is provided a milk suction and collection device that is integrally manufactured and formed by silicone. The milk suction and collection device includes a main body which is hollow inside to define a milk storage chamber. A breast protecting film is provided on a side in a thickness direction of the main body and is configured to be fitted with an outer periphery of a breast. The breast protecting film is provided with a milk collecting port communicating with the milk storage chamber. The main body is also provided with a milk pouring port which is operative to be selectively blocked.

As an exemplary implementation of the milk suction and collection device, a support ring is arranged on and protrudes from an inner wall of the main body. The support ring is arranged at a junction of the main body and the breast protecting film. The support ring has a thickness that is greater than a thickness of the breast protecting film.

As an exemplary implementation of the milk suction and collection device, the inner wall and an outer wall of the main body are both smooth. A junction of the main body and the support ring, a junction of the support ring and the breast protecting film, and corners inside and outside the main body are each implemented as a rounded and smooth transition structure.

As an exemplary implementation of the milk suction and collection device, along a height direction of the main body, a distance between an inner wall above the milk collecting port and an outer edge of a top of the breast protecting film is h1, and a distance between an inner wall below the milk collecting port and an outer edge of a bottom of the breast protecting film is h2, where h1 is smaller than h2.

As an exemplary implementation of the milk suction and collection device, the milk collecting port is an elliptical hole. A semi-major axis of the milk collecting port extends along a width direction of the main body, and a center of the milk collecting port is disposed above and spaced apart from a center of the breast protecting film.

As an exemplary implementation of the milk suction and collection device, the main body is provided with a first side wall and a second side wall that are disposed along a width direction of the main body. The first side wall and the second side wall are each provided with an expressing member that protrudes and faces towards an outside of the milk storage chamber. A distance between the two expressing members is greater than a width of a bottom of the main body and a width of a top of the main body.

As an exemplary implementation of the milk suction and collection device, the width of the bottom of the main body is greater than the width of the top of the main body.

As an exemplary implementation of the milk suction and collection device, the expressing members each have an arcuate structure.

As an exemplary implementation of the milk suction and collection device is provided. A thickness of the expressing members is smaller than a thickness of the main body.

As an exemplary implementation of the milk suction and collection device, the breast protecting film has a shape that matches a shape of the side of the main body on which the breast protecting film is provided; and/or a support ring is arranged on and protrudes from an inner wall of the main body, where the support ring is arranged at a junction of the main body and the breast protecting film, and the support ring has a shape that matches a shape of an outer edge of the breast protecting film.

As an exemplary implementation of the milk suction and collection device, the main body includes a top, a bottom, a first side wall, a second side wall, a front side wall and a rear side wall. The breast protecting film is arranged on the front side wall. The first side wall and the second side wall are spaced apart in the width direction of the main body. The front side wall and the rear side wall are spaced apart in a thickness direction of the main body. The top and the bottom are spaced apart in the height direction of the main body.

The milk pouring port is defined in a center of the top; or the milk pouring port is defined in the rear side wall, and a center of the milk pouring port is located above a center of the milk collecting port; or the milk pouring port is located on the first side wall or the second side wall, and the center of the milk pouring port is located above the center of the milk collecting port.

As an exemplary implementation of the milk suction and collection device, a connecting band is provided on a side of the milk pouring port, and a sealing plug is arranged on and protrudes from the connecting band, and the sealing plug is operative to be inserted into the milk pouring port to seal the milk pouring port.

As an exemplary implementation of the milk suction and collection device, the sealing plug is arranged at a non-end part of the connecting band.

As an exemplary implementation of the milk suction and collection device is provided, the sealing plug includes a connecting rod. A tapered guide member is arranged at an end of the connecting rod that is distal to the connecting band. A larger end of the guide member is connected to the connecting rod. The smaller end of the guide member is suspended. A diameter of the larger end of the guide part is D1. A diameter of the smaller end of the guide part is D2. A diameter of the milk pouring port is d, where the diameter D1 of the larger end of the guide member, the diameter D2 of the smaller end of the guide member, and the diameter of the milk pouring port d satisfy the following relationship: $D2 < d < D1$.

As an exemplary implementation of the milk suction and collection device, the connecting rod is of a tapered shape. A larger end of the connecting rod is connected to the larger end of the guide part. A smaller end of the connecting rod is connected to the connecting band. In response to the sealing plug being inserted into the milk pouring port, the milk pouring port is in interference fit with a non-end part of the connecting rod.

As an exemplary implementation of the milk suction and collection device, the support ring is provided with a guide groove which is arranged along the thickness direction of the support ring in a penetrating manner, allowing the guide groove to communicate spaces on two sides of the support ring, where the guide groove is disposed adjacent to the milk pouring port.

As an exemplary implementation of the milk suction and collection device, the support ring and the breast protecting film form a groove therebetween, and a bottom of the guide groove is flush with a bottom of the groove and with the inner wall of the main body.

As an exemplary implementation of the milk suction and collection device, a height of the milk suction and collection device lies in the range of 90 to 95 mm, a maximum width of the milk suction and collection device lies in the range of 90 to 95 mm, a maximum thickness of the milk suction and collection device lies in the range of 15 to 52 mm, and a net weight of the milk suction and collection device lies in the range of 47 to 57 g.

As an exemplary implementation of the milk suction and collection device, the milk storage chamber has a capacity that lies in the range of 70 to 85 ml.

As an exemplary implementation of the milk suction and collection device, the milk suction and collection device is made of a silicone that has a hardness that lies in the range of 45 to 50 degrees.

As an exemplary implementation of the milk suction and collection device, the bottom of the main body is provided with two set of fixing foot assemblies arranged at two sides of the main body and spaced apart from each other along a thickness direction of the main body. The two sets of fixing foot assemblies include a first assembly arranged at a front side of the main body and a second assembly arranged at a rear side of the main body. The first assembly includes two front fixing feet arranged at intervals along the width direction of the main body. The second assembly includes two rear fixing feet arranged at intervals along the width direction of the main body. The front fixing feet and the rear fixing feet form an acute angle. Embodiments of the present disclosure provide the following beneficial effects. The milk suction and collection device is integrally manufactured and formed by silicone. Thus, the side of the main body of the milk suction and collection device that is provided with the breast protection film can be fitted with the breast. When the milk pouring port is closed, the breast pumping function can be fulfilled by squeezing the main body. When the milk pouring port is closed, the main body can serve the milk collecting function. That is, a single device can achieve the dual function of breast pumping and milk collecting, leading to a high practicability. The milk storage chamber can be used as a breast pumping chamber as well as a milk collecting chamber, thereby greatly simplifying the structure of the milk suction and collection device as well as reducing the size and weight of the milk suction and collection device. Thus, the milk suction and collection device can be hidden under clothes for breast pumping and milk collecting operations making it be able to be used in any public environment. Furthermore, the milk suction and collection device is lightweight, so that the milk suction and collection device can be effectively prevented from falling off under the fitting action of the breast protecting film, allowing the breast pumping and milk collecting operations to be smoothly performed.

BRIEF DESCRIPTION OF DRAWINGS

The present disclosure will be further described in detail below in connection with the drawings and embodiments.

In the drawings: 1. Main body; 11. Milk pouring port; 12. First side wall; 13. Second side wall; 14. Expressing member; 15. Bottom; 16. Top; 17. Rear side wall; 2. Breast protecting film; 21. Milk collecting port; 3. Support ring; 4. Connecting band; 5. Sealing plug; 51. Connecting rod; 52. Guide part; 6. Guide groove; 7. Groove; 8. Front fixing feet; 9. Rear fixing feet.

DETAILED DESCRIPTION

To provide a better understanding for the problems to be solved, solutions adopted, and effects to be achieved by the present disclosure, the solutions of the present disclosure are described in further detail in conjunction with the accompanying drawings and embodiments. The embodiments described below are merely part rather than all of the embodiments of the present disclosure. Based on the embodiments of the present disclosure, all other embodiments obtained by those skilled in the art without making creative efforts shall all fall in the scope of the present disclosure.

In the description of the present disclosure, unless otherwise expressly specified and defined, the terms "connected to each other", "connected", or "fixed" are to be construed in a broad sense, for example, as permanently connected, detachably connected, or integrated; mechanically connected or electrically connected; directly connected to each other or indirectly connected to each other via an intermediary; or internally connected or interactional between two components. For those skilled in the art, the preceding terms can be construed depending on specific contexts.

In the present disclosure, unless otherwise expressly specified and defined, when a first feature is described as "above" or "below" a second feature, the first feature and the second feature may be in direct contact, or be in contact via another feature between the two features. Moreover, when the first feature is described as "on", "above" or "over" the second feature, the first feature is right on or obliquely on the second feature, or the first feature is simply at a horizontally higher level than the second feature. When the first feature is described as "under", "below", or "underneath" the second feature, the first feature is right under, below or underneath the second feature or the first feature is obliquely under, below or underneath the second feature, or the first feature is simply at a lower level than the second feature.

Figure 1:
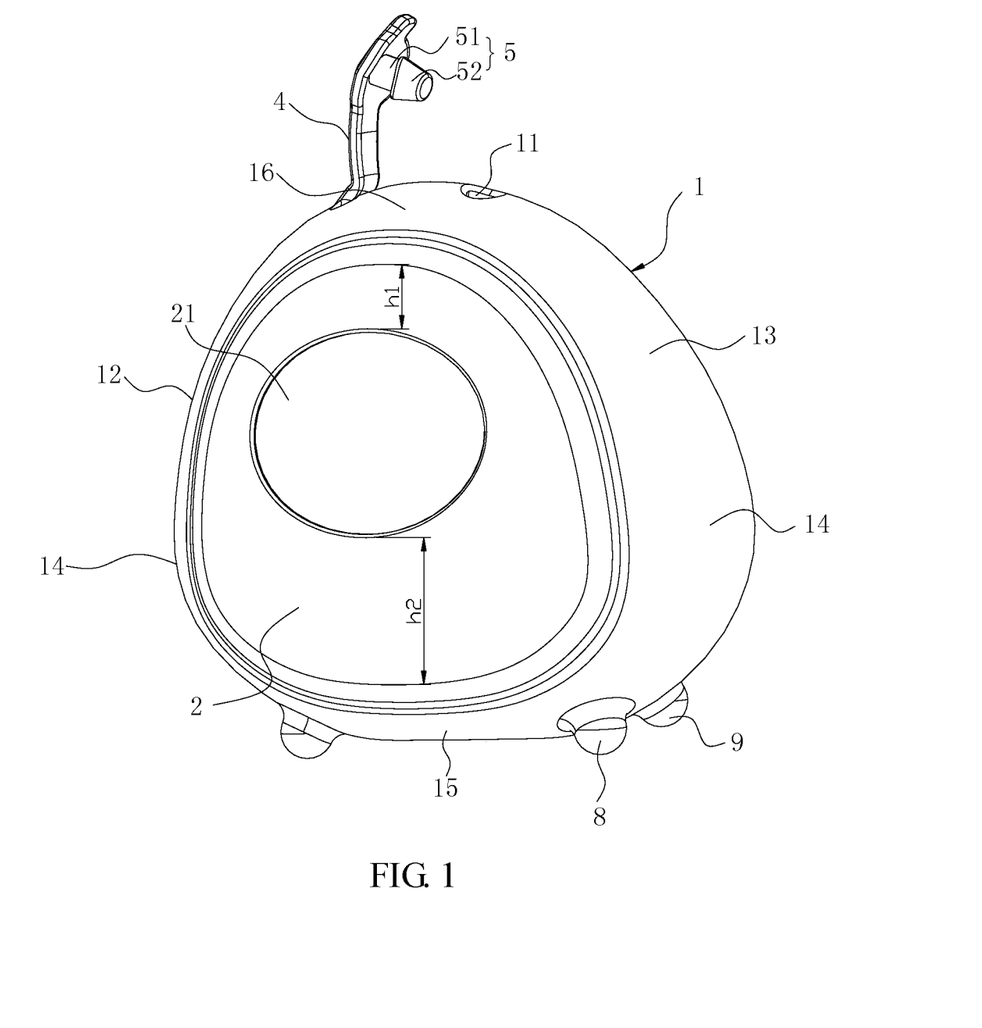
FIG. 1 is a perspective view of a milk suction and collection device observed from a first viewing angle according to an embodiment of the present disclosure.
Figure 2:
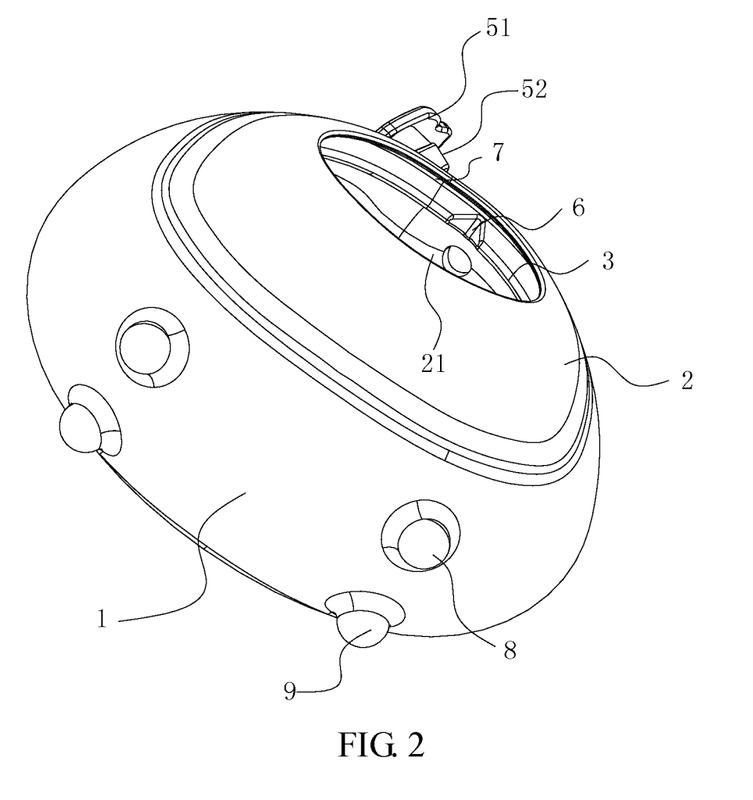
FIG. 2 is a perspective view of a milk suction and collection device observed from a second viewing angle according to an embodiment of the present disclosure.
Figure 3:
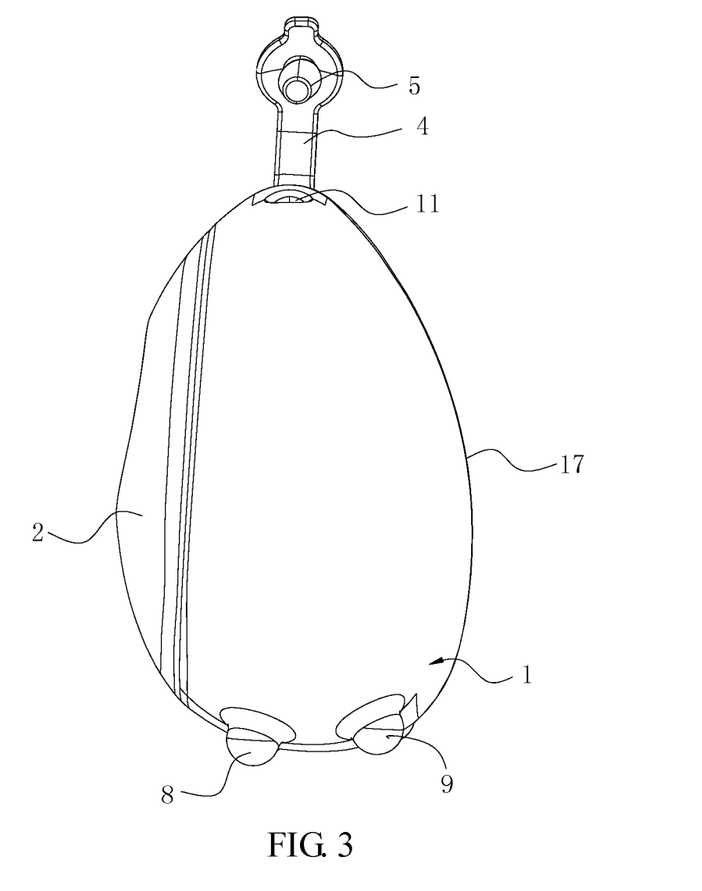
FIG. 3 is a schematic side view of a milk suction and collection device according to an embodiment of the present disclosure.

As illustrated in FIGS. 1 to 3, embodiments of the present disclosure provide a milk suction and collection device. The width direction, the thickness direction, and the height direction of the milk suction and collection device mentioned in the present disclosure are determined depending on the actual state of use. As illustrated in FIG. 1, the X direction in the figure is the thickness direction of the milk suction and collection device. The Y direction in the figure is the width direction of the milk suction and collection device. The Z direction in the figure is the height direction of the milk suction and collection device.

As illustrated in FIGS. 1 to 3, embodiments of the present disclosure provide a milk suction and collection device integrally manufactured and formed by silicone. The milk suction and collection device includes a main body 1. The main body 1 is hollow inside to define a milk storage chamber. A breast protecting film 2 is provided on a side in a thickness direction of the main body and is configured to be fitted with an outer periphery of a breast. The breast protecting film 2 is provided with a milk collecting port 21 communicating with the milk storage chamber. The main body 1 is further provided with a milk pouring port 11 which is operative to be selectively blocked. The milk suction and collection device is integrally manufactured and formed by silicone. Thus, the side of the main body 1 of the milk suction and collection device that is provided with the breast protecting film 2 is fitted with the breast. When the milk pouring port 11 is closed, the breast pumping function can be fulfilled by squeezing the main body 1. When the milk pouring port 11 is opened, the main body can serve the milk collecting function. That is, a single device can achieve the dual function of breast pumping and milk collecting, leading to a high practicability. The milk storage chamber can be used as a breast pumping chamber as well as a milk collecting chamber, thereby greatly simplifying the structure of the milk suction and collection device as well as reducing the size and weight of the milk suction and collection device. Thus, the milk suction and collection device can be hidden under clothes for breast pumping and milk collecting operations making it be able to be used in any public environment. Furthermore, the milk suction and collection device is lightweight, so that the milk suction and collection device can be effectively prevented from falling off under the fitting action of the breast protecting film, allowing the breast pumping and milk collecting operations to be smoothly performed.

In embodiments of the present disclosure, the milk suction and collection device is integrally manufactured and formed by a silicone that has a hardness that lies in the range of 45 to 50 degrees. The silicone has resilience. The characteristic of the silicone determines that the silicone with a stronger rigidity comes together with a larger rebound, and the silicone with a weaker rigidity comes together with a smaller rebound. The following shows comparisons by the principle that silicone can restore its original shape after being squeezed.

Three groups of silicone with different hardnesses are prepared, including: a hardness of 20 to 44 degrees, a hardness of 45 to 50 degrees, and a hardness of 51 to 65 degrees. The evaluation results are as follows.

(1) The milk suction and collection device using the silicone material with the hardness of 20 to 44 degrees has a weak resilience, and the milk storage chamber has a slow rebound and a small suction force. The secretion of the mother's milk is 1 to 3 drops/second, accompanied by a small suction force and slow milk collecting speed. Furthermore, with such hardness the breast protecting film 2 has a low degree of fitness with the breast, such that air leakage is likely to occur and the breast protecting film is easy to fall off from the breast.

(2) The milk suction and collection device using the silicone material with the hardness of 51 to 65 degrees has an enhanced hardness, and the resilience effecting as well as the suction force of the milk storage chamber is increased. The degree of fitness between the breast protecting film 2 with the breast is improved, and so air leakage no longer occurs. However, through actual tests, the secretion of the mother's milk is 8 to 12 drops/second, accompanied by an excessively large suction force thereby easily causing discomfort and even pain to the user's breast. Furthermore, after the hardness of the silicone reaches 51 degrees, the milk suction and collection device become brittle and is vulnerable to damage, thus greatly reducing the durability of the product.

(3) The milk suction and collection device using the hardness in this embodiment (namely 45 to 50 degrees) has a greater deformation, a strong resilience, and a moderate suction force. The fitness degree between the breast protecting film 2 and the breasts is high, and no air leakage and falling cases are discovered. Through actual tests, the secretion of the mother's milk is 4 to 6 drops/second. Performing the breast pumping operation in this state leads to a high breast pumping efficiency and also allows the user to feel comfortable during breast pumping.

Specifically, a height of the milk suction and collection device lies in the range of 90 to 95 mm, a maximum width of the milk suction and collection device lies in the range of 90 to 95 mm, a maximum thickness of the milk suction and collection device lies in the range of 15 to 52 mm, and a net weight of the milk suction and collection device lies in the range of 47 to 57 g. The designed milk suction and collection device has a small overall occupied area, can be directly placed under clothes for milk collecting and breast pumping operations. Because the user's breast is not exposed, the milk suction and collection device can be used in any environment. The volume of the milk storage chamber can also meet the volume range requirements of common electric breast pumps and manual breast pumps available on the market. The volume of the common electric breast pumps and the common manual breast pumps currently available on the market lies in the range of 50 to 120 ml, which can meet the user's requirement for a single breast pumping cycle, thereby reducing the times of pouring milk. In addition, based on the comparison with multiple samples, the milk suction and collection device according to the data described above has a volume of about two-thirds the volume of a manual breast pump and a weight of only two-fifths the weight of a single complete electric breast pump.

The thickness of the breast protecting film 2 is less than the thickness of the main body 1. This design is mainly used for enabling the main body 1 to have a certain strength and preventing the main body 1 from deforming, so that milk in the main body 1 is prevented from overflowing. In this embodiment, the thickness of the main body 1 lies in the range of 4 to 5 mm. Under such thickness, the main body 1 may have enough strength to support the main body 1 enabling it not to deform. The main body 1 can be conveniently squeezed and deformed by a user to create a suction force to pump out milk. Furthermore, under this thickness main body 1 applies the optimal suction force on the breast, ensuring that the secretion of the mother's milk of the breast to be 4 to 6 drops/second with the optimal comfort and minimum damage to the breast.

In one embodiment, a support ring 3 is arranged on and protrudes from an inner wall of the main body 1. The support ring 3 is arranged at a junction of the main body 1 and the breast protecting film 2. The thickness of the support ring 3 is greater than the thickness of the breast protecting film 2. By this configuration, the support ring 3 can provide effective support to the milk collecting port 21 of the milk suction and collection device. The milk collecting port 21 is in contact with the breast, or when the milk suction and collection device is squeezed, this support ring 3 effectively keeps the shape of milk collecting port 21 to be unchangeable. Thus, the breast protecting film 2 is kept fit with the breast.

In this embodiment, the shape of the breast protecting film 2 matches the shape of one side of main body 1 that is provided with the breast protecting film. The shape of the support ring 3 matches the shape of the outer edge of the breast protecting film 2. That is, the breast protecting film 2 and the support ring 3 are scaled in equal proportions relative to the overall shape of the main body 1.

In other embodiments, the breast protecting film 2 apparently can be shaped to not match the overall external dimensions of the main body 1. The support ring 3 can be shaped to match the shape of the outer edge of the breast protecting film 2.

Specifically, along the height direction of the main body 1, a distance between an inner wall above the milk collecting port 21 and an outer edge of a top of the breast protecting film 2 is h1. A distance between an inner wall below the milk collecting port 21 and an outer edge of a bottom of the breast protecting film 2 is h2, where h1 is smaller than h2. The breast of a lactating woman may become larger and drooping. The milk collecting port 21 is disposed at the upper middle part of the breast protecting film 2. When the breast protecting film 2 contact the breast, the width of the latter half of the breast protecting film 2 is greater than the width of the upper half of the breast protecting film 2, thereby creating a stronger upward supporting force to the breast thus lifting the user's drooping breast and holding the nipple at the middle part of milk collecting port 21. As such, the milk suction and collection device according to the present disclosure can be normally used by users of different breast shapes, and the discomfort from the drooping of the user's breast is alleviated at the same time.

Further, the milk collecting port 21 is an elliptical hole. A semi-major axis of the milk collecting port 21 extends along a width direction of the main body, and a center of the milk collecting port 21 is disposed above and spaced apart from a center of the breast protecting film 2. The elliptical milk collecting port 21 can form a smooth burr-free and sharp-angle-free structure, thereby improving the user's comfort of use. The elliptical milk collecting port 21 is disposed at the upper middle position of the breast protecting film 2, so that a relatively ideal accommodating effect can be achieved for the breast, and the breast is prevented from deviating or separating from the breast protecting film 2 in the use.

In this embodiment, the minimum diameter of the milk collecting port 21 is 32 mm, and the maximum diameter of the milk collecting port is 42 mm.

In an embodiment, the inner wall and the outer wall of the main body 1 are both smooth. A junction of the main body 1 and the support ring 3, a junction of the support ring 3 and the breast protecting film 2, and corners inside and outside the main body 1 are all implemented as a rounded and smooth transition structure. This design can prevent both the inside and outside of the main body 1 from forming the dead corners, so that main body 1 can be conveniently washed. Furthermore, the main body 1 can provide increased comfort when held in the user's hand.

In an embodiment, the main body 1 includes a top 16, a bottom 15, a first side wall 12, a second side wall 13, a front side wall and a rear side wall 17. The breast protecting film 2 is provided on the front side wall. The first side wall 12 and the second side wall 13 are spaced apart in the width direction of the main body 1. The front side wall and the rear side wall 17 are spaced apart in a thickness direction of the main body 1. The top 16 and the bottom 15 are spaced apart in the height direction of the main body 1.

The first side wall 12 and the second side wall 13 are each provided with an expressing member 14 that protrudes and faces towards the outside of the milk storage chamber. The distance between the two expressing members 14 is greater than the width of the bottom 15 of the main body 1 and the width of the top 16 of the main body 1. By arranging the expressing members 14 to protrude outwards, on one hand, a user can conveniently squeeze the main body 1 for breast pumping; on the other hand, the volume of the milk storage chamber can be increased.

In this embodiment, the width of the bottom 15 of the main body 1 is greater than the width of the top 16 of the main body 1. This design can form a structure with a narrow upper part and a wide lower part, so that the shape of the milk suction and collection device is more stable.

Specifically, the expressing members 14 have an arcuate structure. This design can enable the outer wall and the inner wall of main body 1 to be free of acute-angled structures, preventing the forming of dead corners. Thus, the main body is convenient to clean. In addition, the expressing members 14 of arcuate structure are more suitable for the squeezing operations.

Further, the thickness of the expressing members 14 is smaller than the thickness of the main body 1. The thin expressing members 14 have better resilience effect. When the expressing members 14 are squeezed, they can create a greater suction force and greater breast pumping speed.

In an embodiment, the milk pouring port 11 is positioned in the center of the top 16. The design can ensure that the milk in the milk storage chamber can be poured out more easily. Apparently, the location of the milk pouring port 11 is not limited to the center of the top 16. The milk pouring port 11 may be located at other locations of the main body 1. For example, the milk pouring port 11 is located in the rear side wall 17, and the center of the milk pouring port 11 is located above the center of the milk collecting port 21. Or, the milk pouring port 11 is located on the first side wall 12 or the second side wall 13, and the center of the milk pouring port 11 is located above the center of the milk collecting port 21.

Specifically, the diameter d of the milk pouring port 11 is 5 mm.

In the embodiment, one side of the milk pouring port 11 is provided with a connecting band 4. A sealing plug 5 is arranged on and protrudes from the connecting band 4, and the sealing plug 5 can be inserted into the milk pouring port 11 to seal the milk pouring port 11. The non-detachable sealing plug 5 can be inserted into the milk pouring port 11 as required to seal the milk pouring port 11. The sealing plug 5 made of silicone has good sealing effect and it is not vulnerable to being lost.

In this embodiment, the sealing plug 5 is provided at a non-end part of the connecting band 4. By this design, the end part of the connecting band 4 would be able to provide sufficient area for pulling operation, so that the sealing plug 5 can be conveniently taken out of the milk pouring port 11, facilitating the port of the milk pouring port 11.

Specifically, the sealing plug 5 includes a connecting rod 51. A tapered guide member 52 is arranged at one end of the connecting rod 51 that is distal to the connection band 4. A larger end of the guide part 52 is connected to the connecting rod 51. A smaller end of the guide part 52 is suspended. A diameter of the larger end of the guide part 52 is D1. A diameter of the smaller end of the guide part 52 is D2. A diameter of the milk pouring port 11 is d. The above diameters D1, D2, and d satisfy the following relationship: D2<d<D1.

In other embodiments, the connecting rod 51 may be tapered. A larger end of the connecting rod 51 is connected to the larger end of the guide part 52. A smaller end of the connecting rod 51 is connected to the connecting band 4. When the sealing plug 5 is inserted into the milk pouring port 11, the milk pouring port 11 would be in an interference fit with the non-end part of the connecting rod 51. By configuring the connecting rod 51 in a tapered structure as well, bidirectional guiding can be achieved by using the tapered connecting rod 51 and the tapered guide member 52, thereby improving the service life of the sealing plug 5.

In an embodiment, the support ring 3 is provided with a guide groove 6. The guide groove 6 is arranged along the thickness direction of the support ring 3 in a penetrating manner, so that the guide groove 6 communicates the spaces on two sides of the support ring 3. The guide groove 6 is adjacent to the milk pouring port 11. Because the support ring 3 is arranged on and protrudes from the inner wall of the main body 1, a groove 7 is formed between the breast protecting film 2 and the support ring 3. Breast can possibly enter the groove 7 during breast pumping and milk collecting. The guide groove 6 can guide the breast in the groove 7. The milk in the groove 7 can be directly guided to the milk pouring port 11 to be poured out when the milk in the main body 1 is poured.

In this embodiment, the bottom of the guide groove 6 is flush with the bottom of the groove 7 and the inner wall of the main body 1 (i.e. the inner wall of the milk storage chamber).

In an embodiment, two sets of fixing foot assemblies are arranged at the bottom 15 of the main body 1. The two sets of fixing foot assemblies are arranged at two sides of the main body 1 and spaced apart from each other along a thickness direction of the main body. The two sets of fixing foot assemblies include a first assembly arranged at a front side of the main body 1 and a second assembly arranged at a rear side of the main body. The first assembly includes two front fixing feet 8 arranged at intervals along the width direction of the main body 1. The second assembly includes two rear fixing feet 9 arranged at intervals along the width direction of the main body 1. The front fixing feet 8 and the rear fixing feet 9 form an acute angle. The two fixed front feet 8 and the two fixed rear feet 9 form four support positions. The four support positions form a rectangular support plane, ensuring the stability of the whole milk suction and collection device.

In this embodiment, the length of the fixed front feet 8 is smaller than the length of the fixed rear feet 9. This design makes the milk suction and collection device to maintain a high level of stability when the milk suction and collection device is full of milk.

Specifically, the fixed front feet 8 and the two fixed rear feet 9 each have a length that lies in the range of 4-6 mm.

The wearable milk suction and collection device made of the integrated silicone has the dual function of breast pumping and milk collecting, and has a small size and a high concealability. The milk suction and collection device provided by the present disclosure can help lactation lactating woman in terms of the following physiological characteristics.

(1) Breast engorgement. The breast pumping effect of the milk suction and collection device can promote the user to secrete milk. For a lactating woman that needs to secrete milk in time, the milk suction and collection device of the present disclosure can promote the milk to continue to be secreted and in larger amounts. The milk suction and collection device has a rounded and smooth design and so can be placed in a woman's most clothes without affecting the user's dressing. Furthermore, it is not easy to be perceived by the people around with a high concealability, so that it is suitable for outdoor use.

(2) Milk leakage. The breast collecting function of the milk suction and collection device can facilitate the user in collecting milk. When a lactating woman is breastfeeding a baby, milk leakage can occur to the breast on the other side because the mammary glands of the human body are communicated with each other. Thus, the milk would be wasted if it is not collected in time. The milk suction and collection device according to the present disclosure adopts an integrally formed structure with a high sealing performance, and it has the dual function of milk suction and milk collecting, thereby achieving the effect of not needing to be handheld. That is, the user can have a good use experience in various states including lying on the back, standing, or walking.

(3) Small amount of milk. The breast pumping function of milk suction and collection device can help stimulate the mammary glands of a user, thereby achieving the milk stimulating effect. Some lactating woman cannot receive timely external stimulation, thus leading to a reduced quantity of milk. The infant is likely to suffer from hypoevolutism if not receiving sufficient nutrition from the mother's milk. By using the milk suction and collection device to create a continuous suction force to the user's breast simulating the sucking effect of a baby, the secretion of mammary glands can be stimulated, the milk yield can be improved, and the situation of a small milk yield of the lactating women can be improved.

In the description of the present disclosure, it is to be understood that the orientational or positional relationships indicated by terms "above" and the like are the orientational or positional relationships shown in the drawings, merely for ease of description and simplifying operations, and these relationships do not indicate or imply that the referred device or component has a specific orientation and is constructed and operated in a specific orientation, and thus it is not to be construed as a limitation to the present disclosure.

In the description of the specification, the description of reference terms "an embodiment" and the like means that specific features, structures, materials or characteristics described in connection with the embodiment are included in at least one embodiment or example of the present disclosure. In the description, the schematic representation of the preceding terms does not necessarily refer to the same embodiment.

Moreover, it will be understood that although this specification is described in terms of the embodiments, not every embodiment includes only one independent solution. Such description mode of the specification is merely for the sake of clarity, and those skilled in the art should regard the specification as a whole. The technical solutions in the embodiments may also be appropriately combined to form other embodiments which will be understood by those skilled in the art.

The principle of the present disclosure is described above in conjunction with the embodiments. The description is merely used for explaining the principle of the present disclosure, and is not intended to explain as limitations to the protection scope of present disclosure in any means. Based on the explanations herein, other embodiments of the present disclosure obtained by those skilled in the art are within the scope of the present disclosure on the premise that no creative work is done.

What is claimed is:

1. A milk suction and collection device, which is integrally manufactured and molded by silicone, the milk suction and collection device comprising:

a main body, which is hollow inside to define a milk storage chamber and which is further provided with a milk pouring port operative to be selectively blocked;

a breast protecting film, provided on a side in a thickness direction of the main body and configured to be fitted with an outer periphery of a breast, wherein the breast protecting film is provided with a milk collecting port communicating with the milk storage chamber, wherein the main body is provided with a first side wall and a second side wall that are disposed along a width direction of the main body, wherein the first side wall and the second side wall are each provided with an expressing member that protrudes and faces towards an outside of the milk storage chamber, and wherein a distance between the two expressing members is greater than a width of a bottom of the main body and a width of a top of the main body.

2. The milk suction and collection device of claim 1, wherein a support ring is arranged on and protrudes from an inner wall of the main body, wherein the support ring is arranged at a junction of the main body and the breast protecting film, and the support ring has a thickness that is greater than a thickness of the breast protecting film.

3. The milk suction and collection device of claim 2, wherein the inner wall and an outer wall of the main body are both smooth, and wherein a junction of the main body and the support ring, a junction of the support ring and the breast protecting film, and corners inside and outside the main body are each a rounded and smooth transition structure.

4. The milk suction and collection device of claim 2, wherein the support ring is provided with a guide groove, which is arranged along the thickness direction of the support ring in a penetrating manner, allowing the guide groove to communicate spaces at two sides of the support ring, wherein the guide groove is disposed adjacent to the milk pouring port.

5. The milk suction and collection device of claim 4, wherein the support ring and the breast protecting film form a groove therebetween, wherein a bottom of the guide groove is flush with a bottom of the groove and with the inner wall of the main body.

6. The milk suction and collection device of claim 1, wherein along a height direction of the main body, a distance between an inner wall above the milk collecting port and an outer edge of a top of the breast protecting film is h1, and a distance between an inner wall below the milk collecting port and an outer edge of a bottom of the breast protecting film is h2, wherein h1 is less than h2.

7. The milk suction and collection device of claim 1, wherein the milk collecting port is an elliptical hole, wherein a semi-major axis of the milk collecting port extends along a width direction of the main body, and a center of the milk collecting port is disposed above and spaced apart from a center of the breast protecting film.

8. The milk suction and collection device of claim 1, wherein the width of the bottom of the main body is greater than the width of the top of the main body.

9. The milk suction and collection device of claim 1, wherein the expressing members each have an arcuate structure.

10. The milk suction and collection device of claim 1, wherein the expressing members each have a thickness that is smaller than a thickness of the main body.

11. The milk suction and collection device of claim 1, wherein the breast protecting film has a shape that matches a shape of the side of the main body on which the breast protecting film is provided; and/or
a support ring is arranged on and protrudes from an inner wall of the main body, wherein the support ring is arranged at a junction of the main body and the breast protecting film, and the support ring has a shape that matches a shape of an outer edge of the breast protecting film.

12. The milk suction and collection device of claim 1, wherein the main body comprises a top, a bottom, front side wall and a rear side wall, wherein the breast protecting film is arranged on the front side wall, the front side wall and the rear side wall are spaced apart in a thickness direction of the main body, and the top and the bottom are spaced apart in the height direction of the main body; wherein the milk pouring port is defined in a center of the top; or the milk pouring port is defined in the rear side wall, and a center of the milk pouring port is located above a center of the milk collecting port; or the milk pouring port is located on the first side wall or the second side wall, and the center of the milk pouring port is located above the center of the milk collecting port.

13. The milk suction and collection device of claim 1, wherein a connecting band is provided on a side of the milk pouring port, and a sealing plug is arranged on and protrudes from the connecting band and is operative to be inserted into the milk pouring port to seal the milk pouring port.

14. The milk suction and collection device of claim 13, wherein the sealing plug is arranged at a non-end part of the connecting band.

15. The milk suction and collection device of claim 13, wherein the sealing plug comprises a connecting rod, wherein a tapered guide member is arranged at an end of the connecting rod that is distal to the connecting band, wherein a larger end of the guide member is connected to the connecting rod, a smaller end of the guide member is suspended, wherein a diameter of the larger end of the guide member is D1, a diameter of the smaller end of the guide member is D2, a diameter of the milk pouring port is d, which satisfy the following relationship: $D2 < d < D1$.

16. The milk suction and collection device of claim 15, wherein the connecting rod is of a tapered shape, a larger end of the connecting rod is connected to the larger end of the guide member, a smaller end of the connecting rod is connected to the connecting band, and in response to the sealing plug being inserted into the milk pouring port, the milk pouring port is in an interference fit with a non-end part of the connecting rod.

17. The milk suction and collection device of claim 1, wherein a height of the milk suction and collection device lies in the range of 90 to 95 mm, a maximum width of the milk suction and collection device lies in the range of 90 to 95 mm, a maximum thickness of the milk suction and collection device lies in the range of 15 to 52 mm, and a net weight of the milk suction and collection device lies in the range of 47 to 57 g.

18. The milk suction and collection device of claim 1, wherein the milk storage chamber has a capacity that lies in the range of 70 to 85 ml.

19. The milk suction and collection device of claim 1, wherein the milk suction and collection device is made of a silicone that has a hardness that lies in the range of 45 to 50 degrees.

20. The milk suction and collection device of claim 1, wherein the bottom of the main body is provided with two set of fixing foot assemblies arranged at two sides of the main body and spaced apart from each other along the thickness direction of the main body, wherein the two sets of fixing foot assemblies comprise a first assembly arranged at a front side of the main body and a second assembly arranged at a rear side of the main body, wherein the first assembly comprises two front fixing feet arranged at intervals along the width direction of the main body, the second assembly comprises two rear fixing feet arranged at intervals along the width direction of the main body, and the front fixing feet and the rear fixing feet form an acute angle.

* * * * *